United States Patent [19]

Rajadhyaksha

[11] Patent Number: 4,461,638
[45] Date of Patent: Jul. 24, 1984

[54] DELIVERY OF PLANT NUTRIENTS

[75] Inventor: Vithal J. Rajadhyaksha, Mission Viejo, Calif.

[73] Assignee: Nelson Research & Development Company, Irvine, Calif.

[21] Appl. No.: 484,024

[22] Filed: Apr. 11, 1983

Related U.S. Application Data

[63] Continuation-in-part of Ser. No. 429,931, Sep. 30, 1982, which is a continuation-in-part of Ser. No. 310,948, Oct. 13, 1981, which is a continuation-in-part of Ser. No. 725,490, Oct. 28, 1976, abandoned, which is a continuation-in-part of Ser. No. 588,247, Jun. 19, 1975, Pat. No. 3,989,816.

[51] Int. Cl.³ .............................................. C05G 3/06
[52] U.S. Cl. ..................................... 71/27; 71/64.01; 71/DIG. 1; 424/181
[58] Field of Search ...................... 71/1, 11, 27, 64.01, 71/64.11, DIG. 1, 115, 95; 424/88, 180, 181, 238, 244, 251

[56] References Cited

U.S. PATENT DOCUMENTS

| | | | |
|---|---|---|---|
| 3,989,816 | 6/1975 | Rajadhyaksha | 424/181 X |
| 4,316,893 | 2/1982 | Rajadhyaksha | 424/180 |
| 4,359,334 | 11/1982 | Brown | 71/95 |
| 4,431,437 | 2/1984 | Kliegman et al. | 71/115 X |

*Primary Examiner*—Ferris H. Lander

[57] ABSTRACT

The disclosure describes compositions and methods for improved delivery of plant nutrients comprising contacting a plant with a composition comprising an effective amount of a plant nutrient and an effective delivery enhancing amount of compound having the structural formula

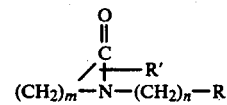

wherein R' is H or a lower alkyl group having 1-4 carbon atoms, m is 3-7, n is 0-17 and R is —CH₃,

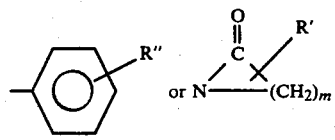

where R" is H or halogen, with the proviso that if m is 3 and R is CH₃, then n is 5-17.

6 Claims, No Drawings

DELIVERY OF PLANT NUTRIENTS

REFERENCE TO EARLIER FILED APPLICATION

This application is a continuation-in-part of U.S. application Ser. No. 429,931 filed Sept. 30, 1982, which in turn is a continuation-in-part of U.S. application Ser. No. 310,948 filed Oct. 13, 1981, which in turn is a continuation-in-part of the U.S. application Ser. No. 725,490 filed Oct. 28, 1976, now abandoned, which in turn is a continuation-in-part of U.S. application Ser. No. 588,247 filed June 19, 1975, now U.S. Pat. No. 3,989,816.

BACKGROUND OF THE INVENTION

1. Field of the Invention

The present invention generally relates to a method of treatment of plants. More particularly, the invention relates to an improved method of delivery of plant nutrients.

2. Background of the Prior Art

The supply and absorption of chemical compounds needed for growth and metabolism may be defined as nutrition and the chemical compounds required by an organism termed nutrients. The mechanisms by which nutrients are converted to cellular material or used for energetic purposes are metabolic processes. The term 'metabolism' encompasses the various reactions occurring in a living cell in order to maintain life and growth. Nutrition and metabolism are thus very closely interreleted.

The essential nutrients required by green plants are exclusively of inorganic nature. In this respect green plants differ fundamentally from man, animals and a number of microorganisms, which additionally need organic compounds as foodstuffs. An essential element may be defined as one which is required for the normal life cycle of an organism and whose functions can not be substituted by other chemical compounds. In addition, the element must be shown to be directly involved in nutrition, as for example as a constituent of an essential enzyme system. Based on this definition, the following chemical elements are now known to be essential for higher plants:

| Carbon | C | Potassium | K | Zinc | Zn |
|--------|---|-----------|---|------|-----|
| Hydrogen | H | Calcium | Ca | Molybdenum | Mo |
| Oxygen | O | Magnesium | Mg | Boron | B |
| Nitrogen | N | Iron | Fe | Chlorine | Cl |
| Phosphorus | P | Manganese | Mn | Sodium | Na |
| Sulphur | S | Copper | Cu | Silicon | Si |
| | | | | Cobalt | Co |

The list of essential elements shown above may well not be complete and other elements, in very low concentrations, may yet be shown to be essential for higher plants. For some microorganisms, for example, vanadium (V) has now been established as an essential element.

The plant nutrients may be divided into macronutrients and micronutrients. Macronutrients are found and needed in plants in relatively higher amounts than micronutrients. The plant tissue content of the macronutrient N, for example is over a thousand times greater than the content of the micronutrient Zn. Following this classification based on the element content in plant material, the following elements may be defined as macronutrients: C, H, O, N, P, S, K, Ca, Mg, Na and Si. The micronutrients are: Fe, Mn, Cu, Zn, Mo, B and Cl. This division of the plant nutrients into macro- and micronutrients is somewhat arbitrary and in many cases differences between the contents of macronutrients and micronutrients are considerably lower than the example cited above.

The process of nutrient uptake and assimilation by plants is not fully understood, although a number of theories of ion uptake and transport are known, see for example, Mengel et al, *Principles of Plant Nutrition*, Chapter 3, "Nutrient Uptake and Assimilation", International Potash Institute, Bern (1978).

SUMMARY OF THE INVENTION

I have now discovered an improved method of delivery of plant nutrients to plants through the use of a compound which, when combined with a plant nutrients, enhances the uptake and assimilation of the plant nutrient in the plant. The composition containing the delivery-enhancing compound and plant nutrient may be applied to the plant in the conventional manner.

The invention, therefore, relates to an improved method of delivery of plant nutrients comprising contacting a plant with a composition comprising an effective amount of a plant nutrient and an effective, delivery-enhancing amount of a compound having the structural formula

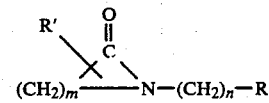

Where R' is H or a lower alkyl group having 1–4 carbon atoms, m is 3–7, n is 0–17, and R is —CH$_3$,

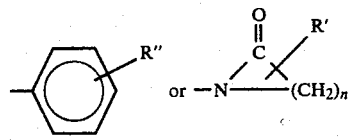

where R" is H or Halogen and R' has the same meaning as above.

The invention also relates to compositions comprising an effective amount of a plant nutrient and an effective, delivery-enhancing amount of a compound having the structural formula

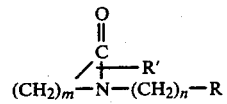

wherein R' is H or a lower alkyl group having 1–4 carbon atoms, m is 3–7, n is 0–17 and R is —CH$_3$,

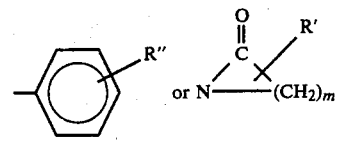

where R" is H or halogen, with the proviso that if m is 3 and R is CH$_3$, then n is 5–17.

In one preferred embodiment, R' is H, m is 5–7, R is CH₃ and n is 0–11. The preferred compound is 1-n-dodecylazacycloheptan-2-one.

DETAILED DESCRIPTION OF THE INVENTION

The 1-substituted azacycloalkan-2-ones used in this invention together with their methods of synthesis are disclosed in U.S. Pat. No. 4,316,893, the relevant portions of which are hereby incorporated by this reference.

The amount of 1-substituted azacycloalkan-2-one which may be used in the present invention is an amount effective for enhancing the delivery of a plant nutrient to a plant. Generally, an effective amount ranges between about 0.01 to about 99.9 and preferably about 0.1 to 10 percent by weight of the composition.

Plant nutrients which may be used in this invention include conventional macronutrients and micronutrients previously described including essential as well as non-essential plant nutrients. Examples of nutrients include, but are not limited to, the primary plant foods: nitrogen including ammonia and nitrate ions, phosphorous (phosphoric acid), potassium (potash); the secondary plant-food elements: calcium, magnesium and sulfur; and the trace elements: manganese, boron, coper, zinc, iron, molybdenum and chlorine. The form of the foregoing nutrients maybe in any conventional form, see, for example, McVickar et al, *Using Commercial Fertilizer*, The Interstate Publishers, Danville, Ill. (1978).

The method of application of the plant nutrient compositions described herein is conventional. See, for example, McVickor et al, *Using Commercial Fertilizers*, Chapter XIV, "Methods of Applying Fertilizers".

The precise amount of the plant nutrient composition to be delivered to the plant will obviously be an effective amount for the desired result expected therefrom. This, of course, will be ascertained by the ordinary skill of the practitioner. Due to enhanced activity which is achieved, the amount of plant nutrients may often be decreased from that generally applicable. In accordance with the usual prudent formulating practices, a dosage near the lower end of the useful range of the particular agent may be employed initially and the dosage increased as indicated from the observed response.

I claim:

1. Method for improved delivery of plant nutrients comprising contacting a plant with a composition comprising an effective amount of a plant nutrient and an effective delivery-enhancing amount of compound having the structural formula

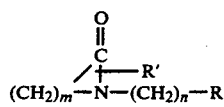

wherein R' is H or a lower alkyl group having 1–4 carbon atoms, m is 3–7, n is 0–17 and R is —CH₃,

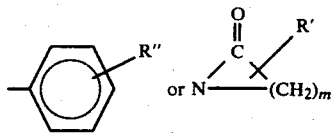

where R" is H or halogen, with the proviso that if m is 3 and R is CH₃, then n is 5–17.

2. A method for improved delivery of plant nutrients comprising contacting a plant with a composition comprising an effective amount of a plant nutrients and an effective delivery-enhancing amount of a compound having the structural formula:

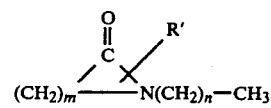

wherein R' is H or a lower alkyl having 1–4 carbon atoms, m is 5–7 and n is 0–11.

3. A method for improved delivery of plant nutrients comprising contacting a plant with a composition comprising an effective amount of a plant nutrients and an effective, delivery enhancing amount of 1-n-dodecylazacycloheptan-2-one.

4. A composition comprising an effective amount of a plant nutrients and an effective, delivery enhancing amount of a compound having the structural formula

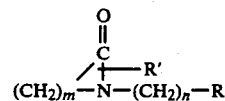

wherein R' is H or a lower alkyl group having 1–4 carbon atoms, m is 3–7, n is 0–17 and R is —CH₃,

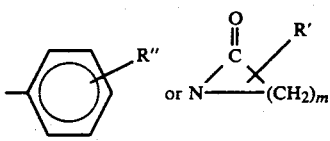

where R" is H or halogen, with the proviso that if m is 3 and R is CH₃, then n is 5–17.

5. A composition comprising an effective amount of a plant nutrient and an effective, delivery-enhancing amount of a compound having the structural formula

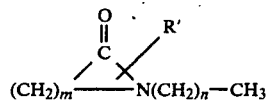

wherein R' is H or a lower alkyl having 1–4 carbon atoms, m is 5–7 and n is 0–11.

6. A composition comprising an effective amount of a plant nutrient and an effective, delivery-enhancing amount of 1-n-dodecylazacycloheptan-2-one.

* * * * *